US005786006A

United States Patent [19]
Lindon et al.

[11] Patent Number: 5,786,006
[45] Date of Patent: Jul. 28, 1998

[54] MINERALIZED DRINKING WATER AND METHOD OF MAKING SAME

[75] Inventors: John A. Lindon, Los Angeles; Arthur Malin, Beverly Hills, both of Calif.

[73] Assignees: Lindon Hearty Water, LLC, Los Angeles; Malin Hearty Water, LLC, Beverly Hills, both of Calif.

[21] Appl. No.: 628,933

[22] Filed: Apr. 8, 1996

[51] Int. Cl.$^6$ .................................................. A23L 1/304
[52] U.S. Cl. .......................... 426/74; 426/590; 426/648
[58] Field of Search ........................... 426/74, 590, 648

[56] References Cited

U.S. PATENT DOCUMENTS

| 4,325,975 | 4/1982 | Lindon et al. | 426/74 |
|---|---|---|---|
| 4,540,584 | 9/1985 | Someya | 426/74 |
| 4,738,856 | 4/1988 | Clark | 426/74 |
| 5,294,606 | 3/1994 | Hastings | 426/74 |

OTHER PUBLICATIONS

Chipperfield et al., "Magnesium and the heart," American Heart Journal, Jun. 1977, vol. 93, No. 6, pp. 679–682.

Dawson et al., "Relationship of metal metabolism to vascular disease mortality rates in Texas," American Journal of Clinical Nutrition, 31, Jul. 1978, pp. 1188–1197.

Neri, "Water hardness and cardiovascular mortality," Annals of the New York Academy of Sciences, 1978 Mar. 30, vol. 304, pp. 203–219.

Karppanen et al., "Minerals, coronary heart disease and sudden coronary death," Adv. Cardiology, 1978, vol. 25, pp. 9–24.

Singh et al., "Magnesium in Atherosclerotic Cardiovascular Disease and Sudden Death," Acta Cardiologica, 1981, vol. 36, No. 6, pp. 411–429.

Masironi, "Geochemistry, soils and cardiovascular disease," Experientia, 1987, Jan. 15, vol. 43, No. 1, pp. 68–74.

Neri et al., "Magnesium and certain other elements and cardiovascular disease," Science of the Total Environment, Mar. 1985, vol. 42, No. 1–2, pp. 49–75.

Lasserre et al., "Should magnesium therapy be considered for the treatment of coronary heart disease? II. Epidemiological evidence in outpatients with and without coronary heart disease," Magneisum Research (1994), vol. 7, 2, pp. 145–153.

Millane et al., "Electrophysiology, Pacing, and Arrhythmia," Clin. Cardio. vol. 16, 1992, pp. 103–108.

Suleiman, "New concepts in the cardioprotective action of magnesium and taurine during the calcium paradox and ischaemia of the heart," Magnesium Research (1994) vol. 7, Nos. 3/4, pp. 295–312.

Prielipp et al., "Magneisum Antagonizes the Actions of Lysophosphatidyl Choline (LPC) in Myocardial Cells: A Possible Mechanism for Its Antiarrhythmic Effects," Anesth Analg 1995, vol. 80, pp. 1083–1087.

Yamaguchi et al., "Preventive effects of magnesium on raised serum lipid peroxide levels and aortic cholesterol deposition in mice fed an atherogenic diet," Magnesium Research (1994) vol. 7, No. 1, pp. 31–37.

Yokoyama et al., Combined effects of magnesium deficiency and an atherogenic level of low density lipoprotein on uptake and metabolism of low density lipoprotein by cultured human endothelial cells. II. Electron microscopic data, Magnesium Research, 1994, Jun., vol. 7, No. 2, pp. 97–105.

Toussaint et al., "Effect of water containing calcium and magneisum sulfates on the elimination of cholesterol in the rat," Archives Internationales de Physiologie et de Biochimie, 1988, vol. 96, pp. 89–100.

Thomas et al., "Serum and erythrocyte magnesium concentrations and migraine," Magnesium Research (1992) vol. 5, No. 2, pp. 127–130.

Sommariva et al., "Prevention of the recurrence of urinary lithias: Mineral water with high or low calcium content," (1987 Dec. 31), 78(24), pp. 1823–1829.

Heaney et al., "Absorbability of the Calcium in a High-Calcium Mineral Water," Osteoporosis International (1994 Nov.); vol. 4, No. 6, pp. 323–324.

Lefebvre et al., "Magnesium and glucose metabolism," Therape, (1994 Jan.–Feb.); vol. 49, No. 1, pp. 1–7.

Anderson, "Chromium Nutrition in the Elderly," Handbook of Nutrition in the Aged, 1994, Chapter 22, pp. 385–392.

Newman et al., "Serum Chromium and Angiographically Determined Coronary Artery Disease," Clinical Chemistry, 1978, vol. 324, No. 4, pp. 541–544.

Simonoff, "Chromium deficiency and cardiovascular risk," Cardiovascular Research, 1984, vol. 18, No. 10, pp. 591–596.

Boyle et al., "Chromium Depletion in the Pathogensis of Diabetes and Athersclerosis," Southern medical Journal, (Dec. 1977), vol. 70, No. 12, pp. 1449–1453.

Abraham et al., "Chromium and Cholesterol–Induced Atherosclerosis in Rabbits," Annals of Nutritional Metabolism, 1991, 35, pp. 203–207.

Karppanen, "Ischaemic Heart Disease An Epidermiological Perspective with Special Reference to Electrolytes," Drugs, (1984 Oct.), 28 Suppl. 1, pp. 17–27.

(List continued on next page.)

*Primary Examiner*—Helen Pratt
*Attorney, Agent, or Firm*—Fulwider Patton Lee & Utecht, LLP

[57] ABSTRACT

An optimal mineralized potable or drinking water formulation. This optimal mineralized drinking water formulation has great utility in preventing cardiovascular disease and improved blood glucose levels, and related blood conditions, and is an aqueous solution consisting essentially of:

0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions.

All the chemical elements are present in the ionic form as water soluble salts, e.g., as sulfates, nitrates, or chlorides or other salts of the elements. The mineral water contains no sodium ions. The minerals can also be in a kit form for adding to water by an end user.

12 Claims, No Drawings

OTHER PUBLICATIONS

Sasaki et al., "Dietary Sodium, Potassium, Saturated Fat, Alcohol, and Stroke Mortality," Stroke (May 1995) vol. 26, No. 5, pp. 783–789.

Liu et al. "The Effects of Dietary Potassium on Vascular and Glomerular Lesions in Hypertensive Rats," Clin. And Exper. Hypertension, (1994), vol., 16, No. 4, pp. 391–414.

Mano et al., "Potassium Accelerates Urinary Sodium Excretion During Salt Loading Without Stimulating Atrial Natriuretic Polypeptide Secretion," Clin. and Experimental Pharmacology and Physiology, (1982), 19, pp. 795–801.

Zhou et al., "The Relationship of Dietary Animal Protein and Electrolytes to Blood Pressure: A Study on Three Chinese Populations," International Journal of Epidemiology, (1994 Aug.), vol. 23, No. 4, pp. 716–722.

Summanen et al., "Does Potassium and Magnesium Supplementation Lower the Blood Pressure of Spontaneously Hypertensive Rats?" Journal of Pharmac Sci, (1994 Feb.), vol. 83, No. 2, pp. 249–251.

Seelig, "Cardiovascular Consequences of Magnesium Deficiency and Loss: Pathogenesis, Prevalence and Manifestations—Magnesium and Chloride Loss in Refractory Potassium Repletion," The American Journal of Cardiology (1989 Apr. 18), vol. 63. No. 14, pp. 4G–21G.

Langford, "Sodium—Potassium Interaction in Hypertension and Hypertensive Cardioovascular Disease," Supplement 1 Hypertension, (1991 Jan.), vol. 17, No. 1, pp. I–156–I–157.

Young et al., "Potassium's cardiovascular protective mechanisms," American Journal of Physiology, (1995 Apr.), 268 (4 pt 2), pp. R825–R837.

Press et al., "The Effect of Chromium Picolinate on Serum Cholesterol and Apolipoprotein Fractions in Human Subjects," Western Journal of Medicine, 1990 Jan., 152(1), pp. 41–50.

Vlad et al., "Concentration of copper, zinc, chromium, iron and nickel in the abdominal aorta of patients deceased with coronary heart disease," Journal of Trace Elements and Electrolytes in Health and Disease, 1994 Jun., 8(2):111–4.

Poulter et al., "A: Low Blood Pressure Populations and the Impact of Rural—Urban Migration," *Textbook of Hypertension*, 1994, pp. 22–36.

Denton, "The effect of increased salt intake on blood pressure of chimpanzees," Nature Medicine, 1995 Oct., vol. 1, No. 10, pp. 1010–1014.

Abbott et al., "Clinical Manifestations of Magnesium Deficiency," Mineral and Electrolyte Metabolism, 1993, vol. 19, pp. 314–322.

McLean et al., "Magnesium and Its Therapeutic Uses: A Review," The American Journal, 1994 Jan., vol. 96, pp. 63–76.

Bubeck et al., "Potentiation of magnesium–deficiency–induced fortotoxicity by concomitant iron deficiency and its prevention by adequate supply via drinking water," Magnesium Research, 1994, vol. 7, 3/4, pp. 245–254.

Anderson et al., "Recent Advances in the Clinical and Biochemical Effects of Chromium Deficiency," Essential and Toxic Trace Elements in Human Health and Disease: An Updake, 1993, pp. 221–234.

MINERALIZED DRINKING WATER AND METHOD OF MAKING SAME

BACKGROUND OF THE INVENTION

There is significant epidemiological evidence found in the scientific literature indicating that the drinking of certain kinds of naturally occurring mineralized waters of one type or another have the effect of decreasing morbidity and mortality due to cardiovascular disease, the major public health problem in the United States and other Western industrialized societies. Examples of the most relevant literature of which we are presently aware attesting to such epidemiological evidence are the following publications:

1) "MAGNESIUM AND THE HEART," American Heart Journal, June, 1977, Vol. 93, No. 6, pp. 679–682, B & J. R. Chipperfield;

2) "RELATIONSHIP OF METAL METABOLISM TO VASCULAR DISEASE MORTALITY RATES IN TEXAS," The American Journal of Clinical Nutrition, 31; July 1978, pp. 1188–1197, E. B. Dawson, M. J. Frey, T. D. Moore and W. J. McGanity;

3) "WATER HARDNESS AND CARDIOVASCULAR MORTALITY," Annals New York Academy of Sciences, 0077-8923/78/0304-0203, pp. 203 -219, Neri and Johansen; 1978;

4) "MINERALS, CORONARY HEART DISEASE AND SUDDEN CORONARY DEATH," Adv. Cardiol. Vol. 25, pp. 9 -24, H. Karppanen et al.; 1978;

5) "MAGNESIUM AND ATHEROSCLEROTIC CARDIOVASCULAR DISEASE AND SUDDEN DEATH," Acta Cardiologica, Vol. 36, 1981.

6) "GEOCHEMISTRY, SOILS AND CARDIOVASCULAR DISEASE" by R. Masironi, Division of Non Communicable Diseases, World Health Organization, Geneva, Switzerland, Experienta, 1987.

7) "MAGNESIUM AND CERTAIN OTHER ELEMENTS AND CARDIOVASCULAR DISEASE" in The Science of Total Environment, Elsevier Science Publishers, Amsterdam, 1985.

8) "SHOULD MAGNESIUM THERAPY BE CONSIDERED FOR THE TREATMENT OF CORONARY HEART DISEASE? II. EPIDEMIOLOGICAL EVIDENCE IN OUTPATIENTS WITH AND WITHOUT CORONARY HEART DISEASE" by B. Lasserre, M. Spoerri, V. Moullet, M. P Theubet in Magnesium Research (1994 June); 7(2):145–53. [Switzerland]

9) "IS HYPOMAGNESEMIA ARRHYTHMOGENIC?" by T. A. Millane, D. E. Ward, A. J. Camm in Clinical Cardiology (1992 February); 15(2):103–8. [London, England.]

10) "NEW CONCEPTS IN THE CARDIOPROTECTIVE ACTION OF MAGNESIUM AND TAURINE DURING THE CALCIUM PARADOX AND ISCHAEMIA OF THE HEART" by M. S. Suleiman in Magnesium Research (1994 December); 7(3–4):295–312. [Bristol, England].

11) "MAGNESIUM ANTAGONIZES THE ACTIONS OF LYSOPHOSPHATIDYL CHOLINES (LPC) IN MYOCARDIAL CELLS: A POSSIBLE MECHANISM FOR ITS ANTIARRHYTHMIC EFFECTS" by R. C. Prielipp, J. F. Butterworth IV, P. R. Roberts, K. W. Black, G. P. Zaloga in Anesthesiology Analog (1995 June); 80(6):1083–7.

12) "PREVENTIVE EFFECTS OF MAGNESIUM ON RAISED SERUM LIPID PEROXIDE LEVELS AND AORTIC CHOLESTEROL DEPOSITION IN MICE FED AN ATHEROGENIC DIET" by Y. Yamaguchi, S. Kitagawa, M. Kunitomo, M. Fijiwara in Magnesium Research (1994 March); 7(1):31–7. [Japan]

13) "COMBINED EFFECTS OF MAGNESIUM DEFICIENCY AND AN ATHEROGENIC LEVEL OF LOW DENSITY-LIPOPROTEIN ON UPTAKE AND METABOLISM OF LOW DENSITY LIPOPROTEIN BY CULTURED HUMAN ENDOTHELIAL CELLS. II. ELECTRON MICROSCOPIC DATA" by S. Yokoyama, J. Gu, K. Kashima, H. I. Nishida, T. L. Smith, F. A. Kummerow in Magnesium Research (1994 June); 7(2):97–105.

14) "EFFECT OF WATER CONTAINING CALCIUM AND MAGNESIUM SULFATES ON THE ELIMINATION OF CHOLESTEROL IN THE RAT" by C. Troussaint, E. Peuchant, C. Courtes, R. Jensen, J. Canellas in Archive of Int. Physiological Biochemistry (1988 June); 96(2):89–100. [Bordeaux, France]

15) "SERUM AND ERYTHROCYTE MAGNESIUM CONCENTRATIONS AND MIGRAINE" by J. Thomas, E. Thomas, E. Tomb in Magnesium Research (1992 June); 5(2):127–30.

16) "PREVENTION OF THE RECURRENCE OF URINARY LITHIASIS: MINERAL WATER WITH HIGH OR LOW CALCIUM CONTENT?" by M. Sommariva, P. Rigatti, M. R. Viola in Minerva Med (1987 Dec. 31); 78(24):1823–9. [Published in Italian. Milan, Italy]

17) "ABSORBABILITY OF THE CALCIUM IN A HIGH CALCIUM MINERAL WATER" by R. P. Heaney, M. S. Dowell in Osteoporosis International (1994 November); 4(6):323–4.

18) "MAGNESIUM AND GLUCOSE METABOLISM" by P. J. Lefebvre, G. Paolisso, A. J. Scheen in Therapie (1994 January–February); 49(1):1–7. [Published in French, Belgium.]

19) "CHROMIUM NUTRITION IN THE ELDERLY" by R. A. Anderson from Vitamin and Mineral Nutrition Laboratory, Beltsville Human Nutrition Research Center, U.S. Department of Agriculture, Agricultural Research Service, Beltsville, Md. in Handbook of Nutrition in the Aged, R. R. Watson, Ed; CRC Press, Boca Raton, Fl., pp. 385–92, 1994.

20) "SERUM CHROMIUM AND ANGIOGRAPHICALLY DETERMINED CORONARY ARTERY DISEASE" by H. A. Newman, R. F. Leighton, R. R. Lanese, N. A. Freeland in Clinical Chemistry (1–78 April) 24(4):541–4.

21) "CHROMIUM DEFICIENCY AND CARDIOVASCULAR RISK" by M. Simonoff in Cardiovascular Research (1984 October); 19(10):591–6.

22) "CHROMIUM DEPLETION IN THE PATHOGENESIS OF DIABETES AND ATHEROSCLEROSIS" by E. Boyle Jr., B. Modschein, H.H. Dash in Southern Medical Journal (1977 December); 70(12):1449–53.

23) "CHROMIUM AND CHOLESTEROL-INDUCED ATHEROSCLEROSIS IN RABBITS" by A. S. Abraham, B. A. Brook, U. Eylath in Annals of Nutritional Metabolism (1991) 35(4):203–7.

24) "ISCHAEMIC HEART DISEASE. AN EPIDEMIOLOGICAL PERSPECTIVE WITH SPECIAL REFERENCE TO ELECTROLYTES" by H. Karppanen in Drugs (1984 October) 28 Suppl 1:17–27.

25) "DIETARY SODIUM, POTASSIUM, SATURATED FAT, ALCOHOL, AND STROKE MORTALITY by S.

Sasaki, X. H. Zhang, H. Kesteloot in Stroke (1995 May) 26(5): 783–9. Belgium.

26) "THE EFFECTS OF DIETARY POTASSIUM ON VASCULAR AND GLOMERULAR LESIONS IN HYPERTENSIVE RATS: by D. T. Liu, M. X. Wang, P. Kincaid-Smith, J. A. Whitworth in Clin Exp Hypertens (1994 July) 16(4):391–414. Australia.

27) "POTASSIUM ACCELERATES URINARY SODIUM EXCRETION DURING SALT LOADING WITHOUT STIMULATING ATRIAL NATRIURETIC POLYPEPTIDE SECRETION" by M. Mano, A. Sugawara, Y. Nara, K. Nakao, R. Horier, J. Endo, J. Imura, Y. Yamori in Clin Exp Parmacol Physiol (1992 December) 19(12):795–801. Japan.

28) "THE RELATIONSHIP OF DIETARY ANIMAL PROTEIN AND ELECTROLYTES TO BLOOD PRESSURE: A STUDY ON THREE CHINESE POPULATIONS" by B. Zhou, X. Zhang, A. Zhu, L. Zhao, S. Zhu, L. Ruan, L. Zhu, S. Liang in International Journal of Epidemiology (1994 August) 23(4):716–22. China.

29) "DOES POTASSIUM AND MAGNESIUM SUPPLEMENTATION LOWER THE BLOOD PRESSURE OF SPONTANEOUSLY HYPERTENSIVE RATS?" by J. O. Summanen, H. J. Vuorela, R. K. Hiltunen in Journal of Pharmac Sci (1994 February) 83(2): 249–51. Finland.

30) "CARDIOVASCULAR CONSEQUENCES OF MAGNESIUM DEFICIENCY AND LOSS: PATHOGENESIS, PREVALENCE AND MANIFESTATIONS—MAGNESIUM AND CHLORIDE LOSS IN REFRACTORY POTASSIUM REPLETION: by M. Seelig in American Journal of Cardiology (1989 April 18) 63(14): 4G–21G.

31) "SODIUM-POTASSIUM INTERACTION IN HYPERTENSION AND HYPERTENSIVE CARDIOVASCULAR DISEASE: by H.G. Langford in Hypertension (1991 January) 17(1 Suppl):I155–7.

32) "POTASSIUM'S CARDIOVASCULAR PROTECTIVE MECHANISMS" by D. B. Young, H. Lin, R. D. McCabe in American Journal of Physiology (1995 April) 268(4 Pt 2): R825–37.

33) "THE EFFECT OF CHROMIUM PICOLINATE ON SERUM CHOLESTEROL AND APOLIPOPROTEIN FRACTIONS IN HUMAN SUBJECTS" by R. R. Press, J. Geller, G. W. Evans in Western Journal of Medicine (1990 January) 152(1):41–5.

34) "CONCENTRATION OF COPPER, ZINC, CHROMIUM, IRON AND NICKEL IN THE ABDOMINAL AORTA OF PATIENTS DECEASED WITH CORONARY HEART DISEASE" by M. Vlad, E. Caseanu, G. Uza, M.Petrescu in Journal of Trace Element Electrolytes Health Disease (1994 June) 8(2):111–4. Romania.

35) "LOW BLOOD PRESSURE POPULATIONS AND THE IMPACT OF RURAL-URBAN MIGRATION" by N. R. Poulter and P. S. Sever in Textbook of Hypertension (Ed.) J. Swales, pp. 22–36, Blackwell Scientific, Oxford 1994.

36) "THE EFFECT OF INCREASED SALT INTAKE ON BLOOD PRESSURE OF CHIMPANZEES" by D. Denton, R. Weisinger, N. Mundy, E. Wickings, A. Dixson, P. Moisson, A. Pingard, R. Shade, D. Carey, R. Ardaillou, F. Paillard, J. Chapman, J. Thillet, J. Michel in Nature Medicine; 1(10), October, 1995. [International study carried out in Australia, Gabon, France, USA]

37) "CLINICAL MANIFESTATIONS OF MAGNESIUM DEFICIENCY" by L. G. Abbott, R. K. Rude in Mineral Electrolyte Metabolism (1993); 19(4–5):314–22.

38) "MAGNESIUM AND ITS THERAPEUTIC USES: A REVIEW" by R. M. McLean in American Journal of Medicine (1994 January); 96(1): 63–76.

39) "POTENTIATION OF MAGNESIUM-DEFICIENCY-INDUCED FOETOTOXICITY BY CONCOMITANT IRON DEFICIENCY AND ITS PREVENTION BY ADEQUATE SUPPLY VIA DRINKING WATER" by J. Bubeck, H. Haussecker, G. Disch, L. Spatling, H. G. Classen in Magnesium Research (1994 December); 7(3–4):245–54.

40) "RECENT ADVANCES IN THE CLINICAL AND BIOCHEMICAL EFFECTS OF CHROMIUM DEFICIENCY" by R. A. Anderson from Vitamin and Mineral Nutrition Laboratory, Beltsville Human Nutrition Research Center, U.S. Department of Agriculture, Agricultural Research Service, Beltsville, Md. in Essential and Toxic Trace Elements in Human Health and Disease: An Update, pp. 221–34, 1993.

Cardiovascular disease is the major public health problem of the U.S. population; 42.5% of deaths from all causes in the United States are from cardiovascular disease (National Center for Health Statistics and the American Heart Association, 1995). The high incidence of cardiovascular disease is significantly related to the insufficient intake of magnesium, calcium, potassium, lithium and chromium salts and the excessive intake of sodium.

In U.S. Pat. No. 4,325,975 "Mineralized Drinking Water and Method of Making Same," the inventors herein obtained patent coverage on a drinking water including magnesium, calcium, lithium and strontium salts. No mention or suggestion was made to include chromium salts or potassium salts.

However, neither the naturally occurring drinking waters of which we are aware nor any manufactured waters provide a formulation for mineralized drinking water which, in our opinion, is an optimum formulation in terms of maximizing the decrease in both the incidence of cardiovascular disease and the morbidity and mortality rate due to cardiovascular disease.

BRIEF SUMMARY OF THE INVENTION

The optimal mineralized drinking water, i.e., potable water formulation, strongly appears to have great utility in preventing cardiovascular diseases and is an aqueous solution consisting essentially of:

0.01–0.08 mg/liter Chromium ion;

30–100 mg/liter Magnesium ions;

30–125 mg/liter Calcium ions;

0.06–0.15 mg/liter Lithium ions; and

10–100 mg/liter Potassium ions.

All the chemical elements are present in the ionic form—as water soluble salts, e.g., as sulfates, nitrates, or chlorides of the elements. The mineral water contains no sodium ions.

This precise combination of ingredients, and the concentration thereof, are believed to be most beneficial in preventing various cardiovascular diseases, especially coronary artery disease, hypertensive heart disease, hypertension, arteriosclerotic and degenerative heart disease, generalized arteriosclerosis, cerebrovascular accidents or strokes, and fatal cardiac arrhythmias.

The literature is voluminous on the advantages of reduced cardiovascular disease fortuitously occurring to those who happen to live in areas of the world which have naturally occurring highly mineralized waters. For example, West Texas is reputed to have both the hardest, most heavily mineralized drinking water and the lowest cardiovascular mortality rates in the United States, a country which has the second highest national cardiovascular mortality rate in the world. See "Relationship of Metal Metabolism to Vascular Disease Mortality Rates in Texas." by E. B. Dawson, et. al. in American Journal of Clinical Nutrition, 1978. However, of the prior art references of which the inventors are aware, none attempt to produce a mineralized potable water which has a zero sodium level, together with a combination of metals (in the form of water-soluble salts thereof) having known positive effects in decreasing the incidence and the effects of cardiovascular disease—and making this mineralized water available to the general public regardless of their geographical location.

Each of the ionic forms of the elements appear to contribute to the prevention of cardiovascular diseases in various ways. The high incidence of cardiovascular disease is significantly related to insufficient intake of magnesium, calcium, potassium and lithium salts, as most people do not live in West Texas, and also an insufficient intake of chromium and an excessive intake of sodium.

Magnesium is the most important ion maintaining the integrity of the human heart; therefore a magnesium deficiency causes less protection against myocardial electrical instability, which can lead to ventricular fibrillation and sudden death. A magnesium deficit predisposes to hypertension and to impaired insulin secretion where magnesium is required for the production of normal insulin. Magnesium deficit leads to elevated circulating dysfunctional insulin, as does a chromium deficiency. The elevated insulin leads to increased atherosclerosis.

A sufficient amount of chromium, like a sufficient amount of magnesium leads to lowering cholesterol, lowering triglycerides and raising high-density cholesterol, the good cardioprotective cholesterol in the blood. A deficiency in either ion causes changes which predispose to increased atherosclerosis; a deficit in both ions compounds the pathology.

Magnesium plays a critical role as the activator of many enzymes such as those concerned with the metabolism of adenosine triphosphate (ATP) and is thus essential for the production and use of energy in human cells. The presence of sufficient magnesium also lessens platelet aggregation.

Potassium supplementation leads to the excretion of excessive fluids and sodium from the body. Potassium also protects against vascular and glomerular lesions. A deficit of potassium together with magnesium accounts for increased myocardial ischaemia and increased myocardial infarctions; also these deficits account for increased hypertension and stroke.

Calcium protects against hypertension and stroke; it also interferes with sodium and fat absorption from the gut. Calcium lowers cholesterol, especially the bad LDL cholesterol.

Lithium lowers blood glucose leading to less circulating insulin which, like magnesium and chromium, protects against atherosclerosis. Lithium, like potassium, is a natural diuretic removing excess sodium and fluids. Lithium in its own way works with magnesium and potassium to reduce hypertension and stroke.

The potable water of the invention provides an ideal vehicle to carry the essential minerals magnesium, calcium, potassium, chromium and lithium in ionic form which is easy to consume and which is easily absorbed into the blood stream.

DESCRIPTION OF THE PREFERRED EMBODIMENT

The mineralized water of this invention consists essentially of the following ingredients, ranges and proportions, viz an aqueous solution of:

0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions.

The optimal formulation lies within the mid range of the limits stated above.

The stated metallic ions are added to distilled water in the form of water soluble salts thereof, e.g., as the sulfates, nitrates, or chlorides. No sodium is added.

One presently preferred method of preparation of the mineralized water of this invention utilizes a distilled water base into which the predetermined concentration of e.g., chromium chloride, magnesium sulfate, calcium chloride, lithium chloride and potassium chloride are added. Other forms of salts can also be utilized.

The resulting mineralized water is then packed in suitable containers for later distribution and use.

It is also within the scope of this invention to prepare the potable mineralized water by simply adding a tablet, capsule pellet or powder containing the water soluble salts of the metals to distilled water in a sufficient amount to produce the aforedescribed concentration limits of metallic ions in the water, i.e., 0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions.

The optimal formulation lies within the mid range of the limits stated above.

The epidemiological evidence indicates that the optimum formulation of mineralized water for daily ingestion purposes, i.e., for use as a drinking water, should not only contain the metallic ions of the foregoing salts but should be devoid of sodium salts. A mineralized water based on this formulation does not appear in nature to the best of our knowledge, yet appears to offer maximum protection against the development and effects of cardiovascular disease.

Various modifications of the inventions will be apparent to those skilled in the art. We intend, therefore, to be bound only by the claims which follow.

We claim:

1. A sodium free mineralized drinking water formulation which consists essentially of an aqueous solution containing:

0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions, each of said ions being present in association with water-soluble salts.

2. The sodium free mineralized drinking water formulation of claim 1, where in said ions are in distilled water.

3. A solid formulation which consists essentially of:

0.01–0.08 parts, by weight, of chromium in a water-soluble salt thereof;

30–100 parts, by weight, of magnesium in a water-soluble salt there of;

30–125 parts, by weight, of calcium in a water-soluble salt thereof;

0.06–0.015 parts, by weight, of lithium in a water-soluble salt there of; and

10–100 parts, by weight, potassium in a water-soluble salt thereof.

4. The solid formulation of claim 3, further comprising 20–40 parts, by weight, of strontium in a water-soluble salt thereof.

5. The solid formulation of claim 3 in tablet form.

6. The solid formulation of claim 3 in a powder form.

7. The solid formulation of claim 3 in a capsule form.

8. The solid formulation of claim 3, which when added to a predetermined volume of distilled water, produces an aqueous solution containing:

0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions.

9. The method of making a potable water which comprises the step of:

adding to distilled water, water-soluble salts consisting essentially of chromium, magnesium, calcium, lithium and potassium in an amount sufficient to produce a concentration range of between:

0.01–0.08 mg/liter Chromium ions;

30–100 mg/liter Magnesium ions;

30–125 mg/liter Calcium ions;

0.06–0.15 mg/liter Lithium ions; and

10–100 mg/liter Potassium ions, in said distilled water.

10. The method of claim 9, wherein said water-soluble salts are added in tablet form.

11. The method of claim 9, wherein said water soluble salts are added in powder form.

12. The method of claim 9, where in said water-soluble salts are added in capsule form.

* * * * *